United States Patent
Pesavento et al.

(10) Patent No.: US 11,020,108 B2
(45) Date of Patent: Jun. 1, 2021

(54) NEEDLE WITH ROUNDED EDGE

(71) Applicant: MOUND LASER & PHOTONICS CENTER, INC., Nashua, NH (US)

(72) Inventors: Paul V. Pesavento, Hutchinson, MN (US); Peter F. Ladwig, Hutchinson, MN (US); Michael W. Davis, Rockford, MN (US); John A. Theget, Hutchinson, MN (US); Kurt C. Swanson, Chippewa Falls, WI (US); Joel B. Michaletz, Litchfield, MN (US); Philip W. Anderson, Dassel, MN (US); Timothy A. McDaniel, Hutchinson, MN (US); Patrick R. LaLonde, Waite Park, MN (US)

(73) Assignee: MOUND LASER & PHOTONICS CENTER, INC., Nashua, NH (US)

( * ) Notice: Subject to any disclaimer, the term of this patent is extended or adjusted under 35 U.S.C. 154(b) by 0 days.

(21) Appl. No.: 16/792,039

(22) Filed: Feb. 14, 2020

(65) Prior Publication Data

US 2020/0180180 A1    Jun. 11, 2020

Related U.S. Application Data

(60) Continuation-in-part of application No. 16/586,791, filed on Sep. 27, 2019, which is a continuation-in-part
(Continued)

(51) Int. Cl.
*A61B 17/06* (2006.01)
*C23F 1/04* (2006.01)
(Continued)

(52) U.S. Cl.
CPC .......... *A61B 17/06066* (2013.01); *C23F 1/04* (2013.01); *B26B 9/00* (2013.01);
(Continued)

(58) Field of Classification Search
CPC .... A61B 17/06066; A61B 2017/00526; A61B 2017/06071; B21G 1/00; B21G 1/003;
(Continued)

(56) References Cited

U.S. PATENT DOCUMENTS

| 3,035,344 A | 5/1962 | Brown |
| 3,696,013 A | 10/1972 | Tafapolsky |

(Continued)

FOREIGN PATENT DOCUMENTS

| EP | 1 284 833 B1 | 7/2010 |
| WO | WO 03/066277 A1 | 8/2003 |

OTHER PUBLICATIONS

Ladwig, Peter F., Sharp Edge Formation Using a Chemical Etching Process, Research Disclosure, Hutchinson Technololgy Incorporated 566007, May 4, 2011, 1 page.
(Continued)

*Primary Examiner* — Robert A Lynch
(74) *Attorney, Agent, or Firm* — McLane Middleton, Professional Association

(57) ABSTRACT

A chemically etched needle is provided herein. The chemically etched needle includes a metal base having a first side and a second side. The chemically etched needle also includes a chemically etched blade at one end of the metal base and formed at an intersection of a distal diverging surface and a proximal diverging surface, at least one of the diverging surfaces slopes inward towards the second side.

14 Claims, 5 Drawing Sheets

Related U.S. Application Data of application No. 15/845,351, filed on Dec. 18, 2017, now Pat. No. 10,478,984, which is a division of application No. 15/057,541, filed on Mar. 1, 2016, now Pat. No. 9,844,888.

(60) Provisional application No. 62/806,586, filed on Feb. 15, 2019, provisional application No. 62/738,756, filed on Sep. 28, 2018, provisional application No. 62/127,083, filed on Mar. 2, 2015.

(51) Int. Cl.
  *B26D 1/00* (2006.01)
  *B26B 9/02* (2006.01)
  *B26B 9/00* (2006.01)

(52) U.S. Cl.
  CPC .............. *B26B 9/02* (2013.01); *B26D 1/0006* (2013.01); *B26D 2001/0053* (2013.01)

(58) Field of Classification Search
  CPC ... B21G 1/006; B26D 2001/0053; C23F 1/00; C23F 1/02; C23F 1/04; G03F 7/00
  See application file for complete search history.

(56) References Cited

U.S. PATENT DOCUMENTS

| | | | |
|---|---|---|---|
| 4,647,300 A | | 3/1987 | Sheets |
| 4,793,218 A | | 12/1988 | Jordan et al. |
| 4,823,467 A | | 4/1989 | Campbell et al. |
| 5,057,401 A | * | 10/1991 | Borysko .......... A61B 17/06066 163/4 |
| 5,100,506 A | | 3/1992 | Sturtevant et al. |
| 5,216,812 A | | 6/1993 | Lyons |
| 5,317,938 A | | 6/1994 | de Juan, Jr. et al. |
| 5,689,889 A | | 11/1997 | Overholt |
| 5,693,454 A | | 12/1997 | Munoz |
| 5,797,961 A | * | 8/1998 | Smith .............. A61B 17/06066 112/222 |
| 5,842,387 A | | 12/1998 | Marcus et al. |
| 6,301,867 B1 | | 10/2001 | Rickheim |
| 6,500,187 B1 | | 12/2002 | Petersen |
| 8,061,237 B2 | | 11/2011 | Hobbs et al. |
| 8,322,253 B2 | | 12/2012 | Howells |
| 9,844,888 B2 | | 12/2017 | Pesavento et al. |
| 10,478,984 B2 | | 11/2019 | Pesavento et al. |
| 10,500,748 B2 | | 12/2019 | Pesavento et al. |
| 10,869,715 B2 | | 12/2020 | Stamm et al. |
| 2004/0098048 A1 | * | 5/2004 | Cunningham ... A61B 17/06066 606/223 |
| 2004/0226176 A1 | | 11/2004 | Peterlin |
| 2005/0115084 A1 | | 6/2005 | Hasegawa |
| 2005/0132581 A1 | | 6/2005 | Jessing |
| 2005/0161429 A1 | | 7/2005 | Sauciunac |
| 2007/0283578 A1 | | 12/2007 | Newman |
| 2009/0217537 A1 | | 9/2009 | Macdonald et al. |
| 2010/0023041 A1 | | 1/2010 | Satake et al. |
| 2010/0140212 A1 | | 6/2010 | Li |
| 2012/0116437 A1 | | 5/2012 | Hörauf |
| 2013/0184609 A1 | | 7/2013 | Lee et al. |
| 2016/0257006 A1 | * | 9/2016 | Pesavento ............ B26D 1/0006 |
| 2016/0257011 A1 | | 9/2016 | Pesavento et al. |
| 2018/0104837 A1 | | 4/2018 | Pesavento et al. |
| 2020/0023534 A1 | | 1/2020 | Pesavento et al. |
| 2020/0139567 A1 | | 5/2020 | Pesavento et al. |
| 2020/0180180 A1 | | 6/2020 | Pesavento et al. |

OTHER PUBLICATIONS

Mantra Public Relations, "Cutting Edge Technology Gets Even Sharper", New York, NY, Jun. 28, 2010, 2 pages.
Precision Micro, New Approach to Medical Saw Blade Production [online], Aug. 28, 2013 [retrieved on Sep. 13, 2016], Retrieved from the Internet <https://www.mdtmag.com/news/2013/08/new-approach-medical-saw-blade-production>, 3 pages.
Office Action in U.S. Appl. No. 15/057,541, dated Feb. 10, 2017.
Notice of Allowance in U.S. Appl. No. 15/057,541, dated Aug. 11, 2017.
Office Action in U.S. Appl. No. 15/057,674, dated Aug. 9, 2017.
Office Action in U.S. Appl. No. 15/057,674, dated Feb. 1, 2018.
Office Action in U.S. Appl. No. 15/057,674, dated Aug. 27, 2018.
Office Action in U.S. Appl. No. 15/057,674, dated Apr. 9, 2019.
Notice of Allowance in U.S. Appl. No. 15/057,674, dated Aug. 6, 2019.
Office Action in U.S. Appl. No. 15/845,351, dated Nov. 19, 2018.
Office Action in U.S. Appl. No. 15/845,351, dated Apr. 30, 2019.
Notice of Allowance in U.S. Appl. No. 15/845,351, dated Jul. 10, 2019.
Office Action in U.S. Appl. No. 16/687,588, dated Jun. 19, 2020.
Pesavento et al., International Application No. PCT/US2020/052907 filed filed Sep. 25, 2020.
International Search Report and Written Opinion dated Jan. 27, 2021 received in PCT application No. PCT/US2020/052907.

* cited by examiner

NEEDLE WITH ROUNDED EDGE

CROSS REFERENCE TO RELATED APPLICATIONS

This application claims the benefit of U.S. Provisional Application 62/806,586, filed Feb. 15, 2019, titled NEEDLE WITH ROUNDED EDGE, and is a Continuation-in-Part of U.S. patent application Ser. No. 16/586,791, filed Sep. 27, 2019, titled CHEMICALLY SHARPENING BLADES, which claims the benefit of U.S. Provisional Application No. 62/738,756, filed Sep. 28, 2018, titled CHEMICALLY SHARPENING BLADES, and is a Continuation-in-Part of U.S. patent application Ser. No. 15/845,351, filed Dec. 18, 2017, titled CHEMICALLY SHARPENING BLADES, now U.S. Pat. No. 10,478,984, which is a Divisional of U.S. patent application Ser. No. 15/057,541, filed Mar. 1, 2016, titled CHEMICALLY SHARPENING BLADES, now U.S. Pat. No. 9,844,888, which claims the benefit of U.S. Provisional Application No. 62/127,083, filed on Mar. 2, 2015, titled CHEMICALLY SHARPENED BLADES, all of which are incorporated by reference herein in their entirety and for all purposes.

FIELD OF THE INVENTION

The invention relates generally to embodiments of a needle and methods of manufacturing, and more particularly, but without limitation to manufacturing embodiments of a needle.

BACKGROUND

A common feature among metallic devices includes edges that have high geometric aspect ratio in two dimensions, as in needles. Often times these sharp edge device features are used to cut or pierce another material, such as paper, metal, wood, plastic or human and animal tissue. Sharpened edges are common features across a wide variety of device applications and product types.

The conventional process for preparing needles from raw stock typically includes straightening spooled wire stock, cutting needle blanks from raw stock, tapering or grinding points on one end of the needle blank, providing a bore for receiving suture thread at the other end of the blank, flat pressing a portion of the needle barrel to facilitate easier grasping by surgical instrumentation, and curving the needle blank.

Most surgical needles are typically made one at a time. However, it is increasingly difficult to maintain the precision quality of very small needles, e.g. needles used in microscopic surgery, such as ophthalmic needles. Each needle must be cut, formed and sharpened, in order to yield uniform surgical needles.

Common methods for fabricating sharpened edges are mechanical processes including brittle cleavage or fracture, machining, grinding, and honing. These processes remove material to fabricate the sharpened edge by breaking bonds with an applied mechanical force. This force is usually applied by direct contact of the workpiece with a tool or another material sharp edge formation technique. This heat can lead microstructural or crystallographic changes that degrade the hardness of the material at the sharpened edge. This unintended tempering or annealing may result in sharpened edges that quickly become dull in use. Mechanical sharpening methods become more involved or more complex when the desired sharpened edge is serrated, curved, wavy, or otherwise non-linear.

SUMMARY

A chemically etched needle is provided herein. The chemically etched needle includes a metal base having a first side and a second side. The chemically etched needle also includes a chemically etched blade at one end of the metal base and formed at an intersection of a distal diverging surface and a proximal diverging surface, at least one of the diverging surfaces slopes inward towards the second side.

In some example embodiments, the at least one of the diverging surfaces includes one or more concave portions formed by etching the metal base through at least one variable permeability mask. The at least one variable permeability mask can include a mask having a comb profile. The first side of the chemically etched needle and the second side of the chemically needle is not symmetric about a centerline of the metal base. In some example embodiments, the metal base is a stainless-steel metal base.

In some example embodiments, the chemically etched needle also includes a rounded edge at the intersection of the second side of the chemically etched needle and the distal diverging surface. The rounded edge was formed by etching the metal base through at least one variable permeability mask.

In some example embodiments, the chemically etched needle also includes a rounded edge at the intersection of the first side of the chemically etched needle and the distal diverging surface. The rounded edge was formed by etching the metal base through at least one variable permeability mask.

In some example embodiments, the chemically etched needle also includes a rounded edge at the intersection of the second side of the chemically etched needle and the proximal diverging surface. The rounded edge was formed by etching the metal base through at least one variable permeability mask.

In some example embodiments, the chemically etched needle also includes a rounded edge at the intersection of the first side of the chemically etched needle and the proximal diverging surface. The rounded edge was formed by etching the metal base through at least one variable permeability mask.

In some example embodiments, a thickness of the metal base is less than about 1000 micrometers. The thickness of the metal base can be less than about 500 micrometers. In some examples, a thickness of the metal base is between about 250 micrometers and about 500 micrometers. The thickness of the metal base is between about 250 micrometers and about 500 micrometers. In some examples, at least one of the diverging surfaces includes one or more concave portions.

A method for forming a needle with one or more round edges is provided herein. The method includes forming one or more masks on a metal base. In some embodiments, the metal base having a first side and a second side. The method also includes chemically etching the masked metal base to form a rounded edge at the intersection of the first side and a first diverging surface.

The method also includes chemically etching the masked metal base to form a rounded edge at the intersection of the second side and the first diverging surface. The method can also include chemically etching the masked metal base to form a rounded edge at the intersection of the first side and a second diverging surface. In some embodiments, the method can also include chemically etching the masked metal base to form a rounded edge at the intersection of the second side and the second diverging surface.

While multiple examples are disclosed, still other examples of the present disclosure will become apparent to those skilled in the art from the following detailed description, which shows and describes illustrative examples of this disclosure. Accordingly, the drawings and detailed description are to be regarded as illustrative in nature and not restrictive.

BRIEF DESCRIPTION OF THE DRAWINGS

FIG. 3A illustrates a cutting device with selectively rounded edges, according to an example of this disclosure.

FIG. 4A illustrates a cutting device with selectively rounded edges, according to an example of this disclosure.

DETAILED DESCRIPTION

Needles with one or more rounded edges and methods for manufacturing are described. An example of an application for a needle with one or more rounded edges includes being used for a diabetic sensor insertion needle used for continuous glucose monitoring. For some embodiments a needle is a component in a single use device for insertion.

Needles according to embodiments described herein enable less trauma during the insertion process. For example, when used with a diabetic sensor stability is not sufficient for use for several hours after insertion with current needles. This lag time is suspected to be caused by trauma during the insertion process. Sharp edges on the needle away from the tip are suspected to be the cause of tissue trauma. Edge rounding eliminates the sharp areas on the sides of the needle, thereby reducing the unwanted cutting during insertion. The disclosed embodiments illustrate the novel configurability to manufacture needles with rounded edges, and/or selective rounded edges.

Figure 1:
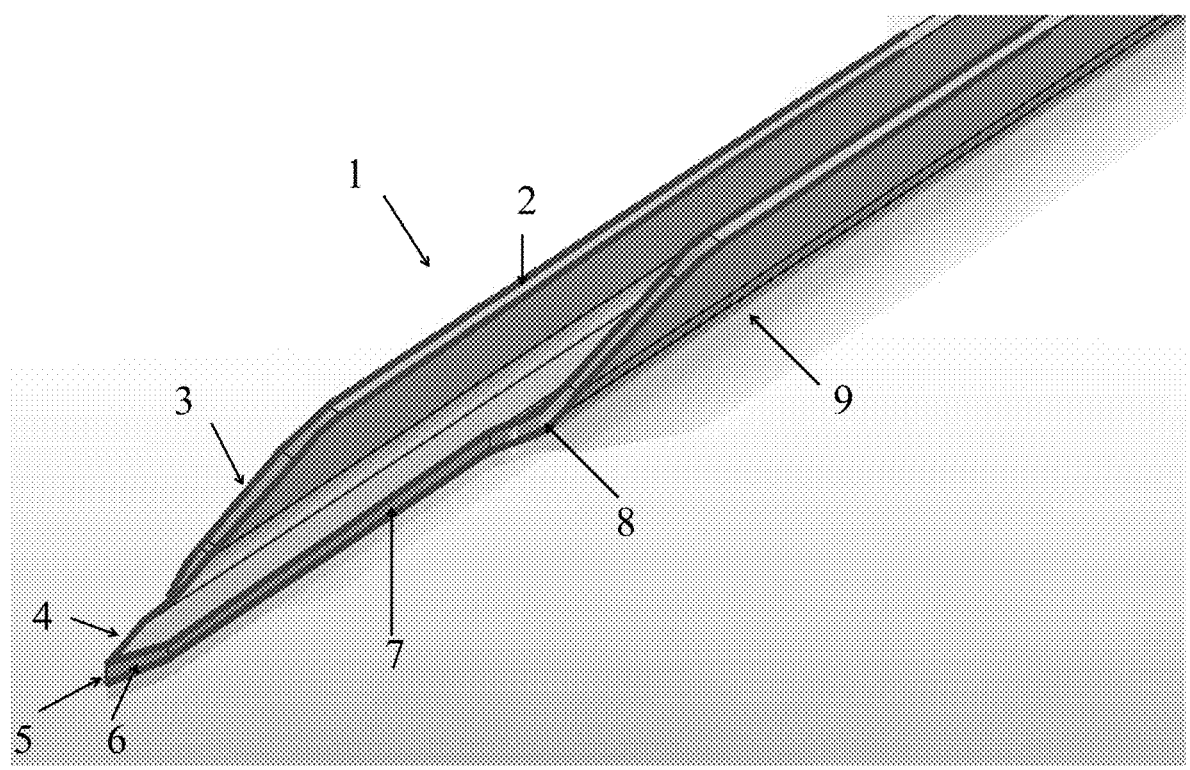
FIG. 1 illustrates a cutting device, according to an example of this disclosure.

FIG. 1 illustrates a cutting device 1 in accordance to an embodiment of the disclosure. The cutting device 1 includes a blade 5 and a main body 9. The main body 9 includes a distal leading edge 2, and a proximal leading edge 7. The distal leading edge 2 can include an incline edge 3. The proximal leading edge 7 can include an inflection point 8 leading to an incline edge. The position of the inflection point 8 can vary along the proximal leading edge 7. For some embodiments, the distal leading edge 2 also includes an inflection point.

The blade 5 is positioned at the end of the cutting device 1, such as at the cutting edge of the cutting device 1. A distal diverging surface 4 and a proximal diverging surface 6 can form at the blade 5. The cutting device 1 can be formed from metal, such as stainless steel, however other types of metals are possible. The cutting device 1 can be a unitary metal body. For example, as further explained herein, a single metal sheet can be chemically etched to form the cutting device 1 (and possibly multiple cutting tools). According to some embodiments, each surface of the cutting device 1 is rounded. For example, the distal leading edge 2, the incline edge 3, the distal diverging surface 4, the proximal diverging surface 6, the proximal leading edge 7, and the inflection point 8 can be formed with rounded edges.

Figure 2:
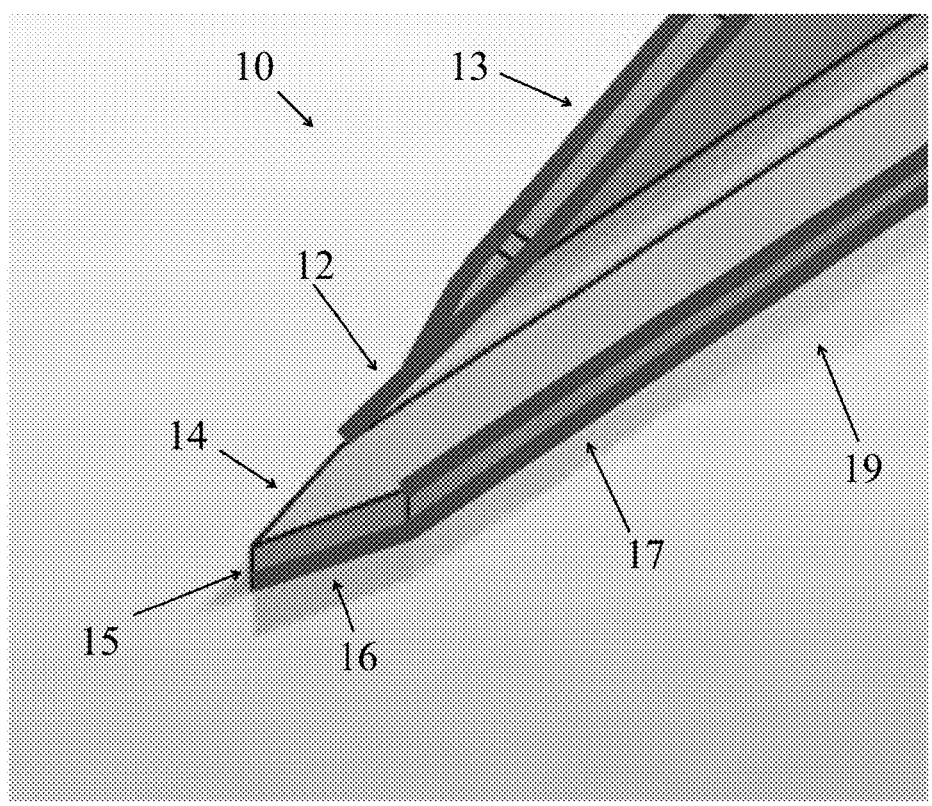
FIG. 2 illustrates a cutting device, according to an example of this disclosure.

FIG. 2 illustrates a cutting device 10 in accordance to an embodiment of the disclosure. The cutting device 10 includes edges that are selectively rounded. The cutting device 10 includes a blade 15 and a main body 19. The main body 19 includes a distal leading edge 12, and a proximal leading edge 17. The distal leading edge 12 can include an incline edge 13. The distal leading edge 12 can also include an inflection point.

The blade 15 is positioned at the end of the cutting device 10, such as at the cutting edge of the cutting device 10. A distal diverging surface 14 and a proximal diverging surface 16 can form at the blade 15. The proximal diverging surface 16 includes edges that are selectively rounded.

FIG. 3A illustrates a cutting device 20 with selectively rounded edges in accordance to an embodiment of the disclosure. The cutting device 20 includes a blade 25 and a main body 29. The main body 29 includes a distal leading edge 22, and a proximal leading edge 27. The distal leading edge 22 can include an incline edge 23. The distal leading edge 22 includes an inflection point.

The blade 25 is positioned at the end of the cutting device 20, such as at the cutting edge of the cutting device 20. A distal diverging surface 24 and a proximal diverging surface 26 can form at the blade 25. The proximal diverging surface 26 includes edges that are selectively rounded.

Figure 3B:
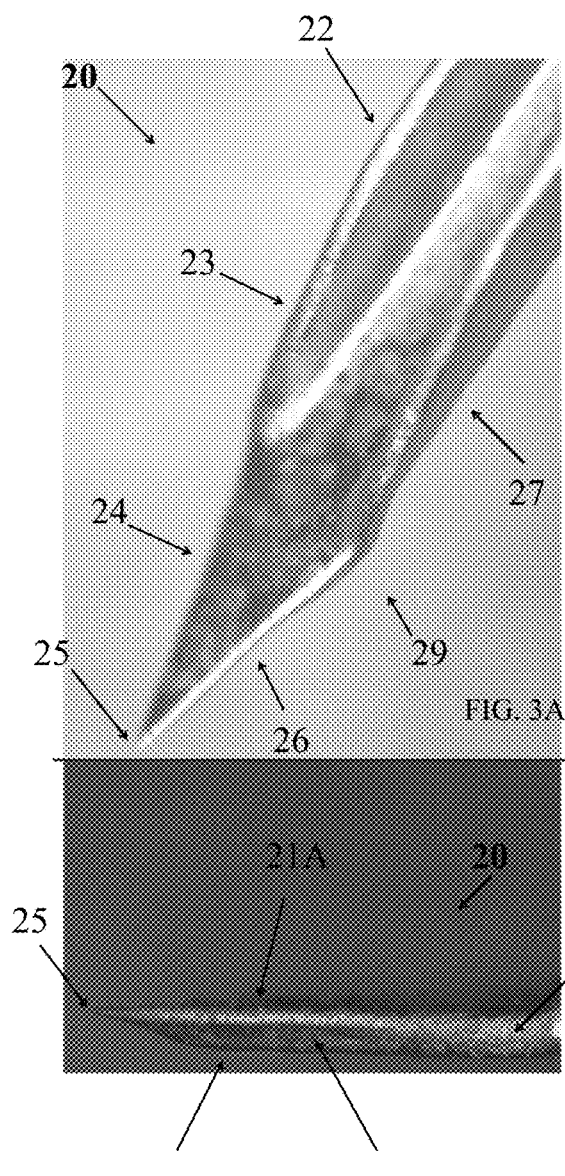
FIG. 3B illustrates a proximal side profile of the blade of cutting device, according to an example of this disclosure.

FIG. 3B illustrates a proximal side profile of the blade of cutting device 20, in accordance with an embodiment of the disclosure. The cutting device 20 has a top surface 21A and a bottom surface 21B. The proximal diverging surface 26 is adjacent to the top surface 21A and the bottom surface 21B of the cutting device 20. The joining of the proximal diverging surface 26 and the top surface 21A is rounded. Similarly, the joining of the proximal diverging surface 26 and the bottom surface 21B is rounded. The proximal diverging surface 26 can include a concave profile, such that the proximal diverging surface 26 slopes inward towards the bottom surface 21B. The proximal leading edge 27 is rounded where the proximal leading edge 27 meets the top surface 21A and the bottom surface 21B. It should be understood that the distal diverging surface may include a similar profile. The complex profile of the cutting device 20, specifically the proximal diverging surface 26, is formed from a multi-stage etching process including remasking between etching stages, e.g., as described with respect to FIGS. 6-7.

FIG. 4A illustrates a cutting device 30 with selectively rounded edges in accordance to an alternative embodiment of the disclosure. The cutting device 30 includes a blade 35 and a main body 39. The main body 39 includes a distal leading edge 32, and a proximal leading edge 37. The distal leading edge 32 can include an incline edge 33. The distal leading edge 32 can include also include an inflection point.

The blade 35 is positioned at the end of the cutting device 30, such as at the cutting edge of the cutting device 30. A distal diverging surface 34 and a proximal diverging surface 36 can form at the blade 35. The proximal diverging surface 36 includes at least one edge that is selectively rounded.

Figure 4B:
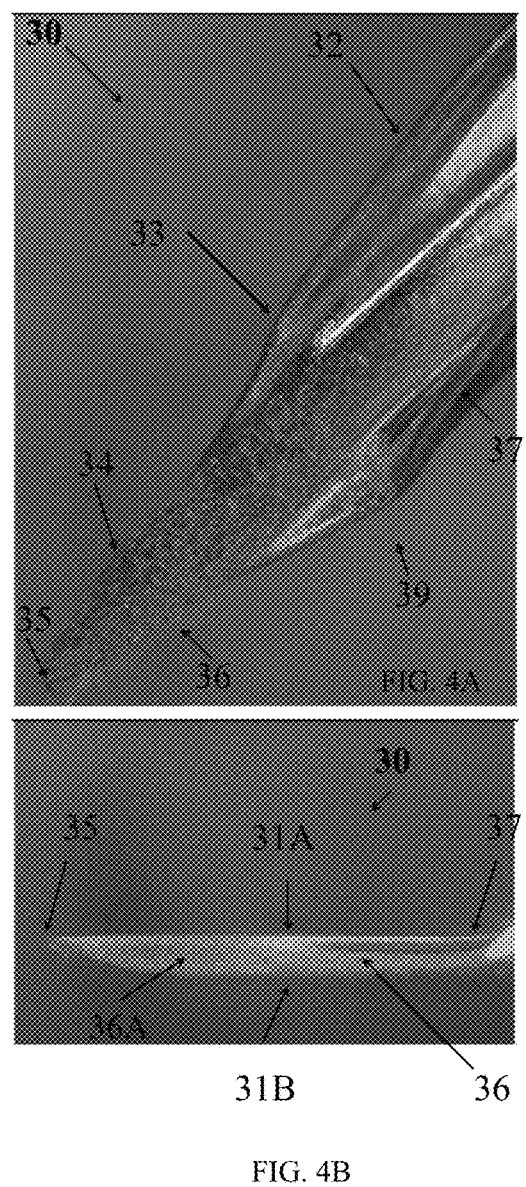
FIG. 4B illustrates a proximal side profile of the blade of cutting device, according to an example of this disclosure.

FIG. 4B illustrates a proximal side profile of the blade of cutting device 30, in accordance with an embodiment of the disclosure. The cutting device 30 has a top surface 31A and a bottom surface 31B. The proximal diverging surface 36 is adjacent to the top surface 31A and the bottom surface 31B of the cutting device 30. The joining of the proximal diverging surface 36 and the top surface 31A is non-rounded, or otherwise angled.

The joining of the proximal diverging surface 36 and the bottom surface 31B is selectively rounded. The proximal diverging surface 36 can include a concave profile 36A, such that the proximal diverging surface 36 slopes inward towards the bottom surface 31B. It should be understood that the distal diverging surface may include a similar profile. The complex profile of the cutting device 30, specifically the proximal diverging surface 36, is formed from a multi-stage etching process including remasking between etching stages, e.g., as described with respect to FIGS. 6-7.

Figures 5A, 5B:
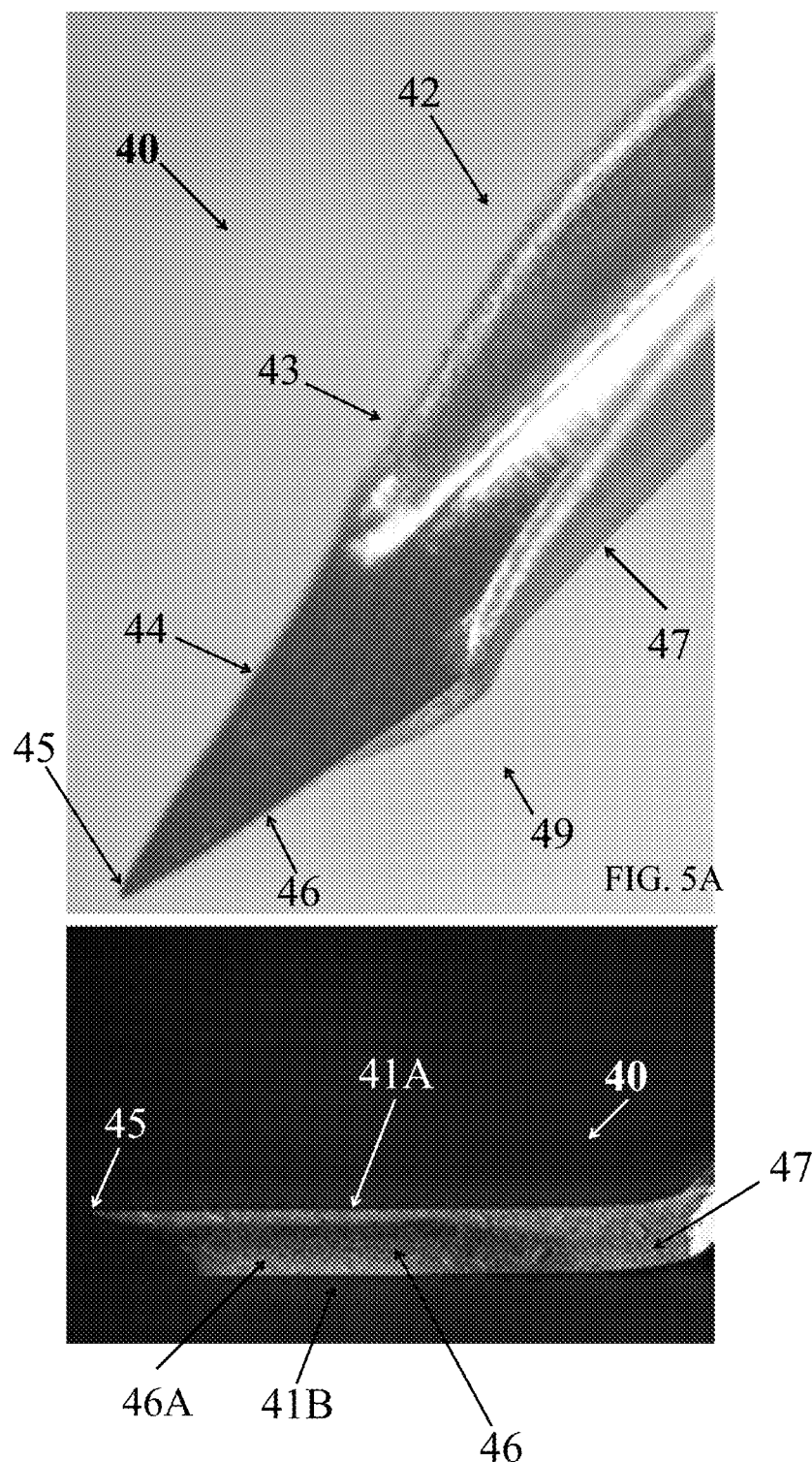
FIG. 5A illustrates a cutting device with selectively rounded edges, according to an example of this disclosure.
FIG. 5B illustrates a proximal side profile of the blade of cutting device, according to an example of this disclosure.

FIG. 5A illustrates a cutting device 40 with selectively rounded edges in accordance to an alternative embodiment of the disclosure. The cutting device 40 includes a blade 45 and a main body 49. The main body 49 includes a distal leading edge 42, and a proximal leading edge 47. The distal leading edge 42 can include an incline edge 43. The distal leading edge 42 can include also include an inflection point.

The blade 45 is positioned at the end of the cutting device 40, such as at the cutting edge of the cutting device 40. A distal diverging surface 44 and a proximal diverging surface 46 can form at the blade 45. The proximal diverging surface 46 includes edges that are non-rounded, or otherwise angled.

FIG. 5B illustrates a proximal side profile of the blade of cutting device 40, in accordance with an embodiment of the disclosure. The cutting device 40 has a top surface 41A and a bottom surface 41B. The proximal diverging surface 46 is adjacent to the top surface 41A and the bottom surface 41B of the cutting device 40. The joining of the proximal diverging surface 46 and the top surface 41A is non-rounded, or otherwise angled.

Similarly, the joining of the proximal diverging surface 46 and the bottom surface 41B is non-rounded, or otherwise angled. The proximal diverging surface 46 can include a concave profile 46A, such that the proximal diverging surface 46 slopes inward towards the bottom surface 41B. It should be understood that the distal diverging surface may include a similar profile. The complex profile of the cutting device 40, specifically the proximal diverging surface 46, is formed from a multi-stage etching process including remasking between etching stages, e.g., as described with respect to FIGS. 6-7.

Figure 6:
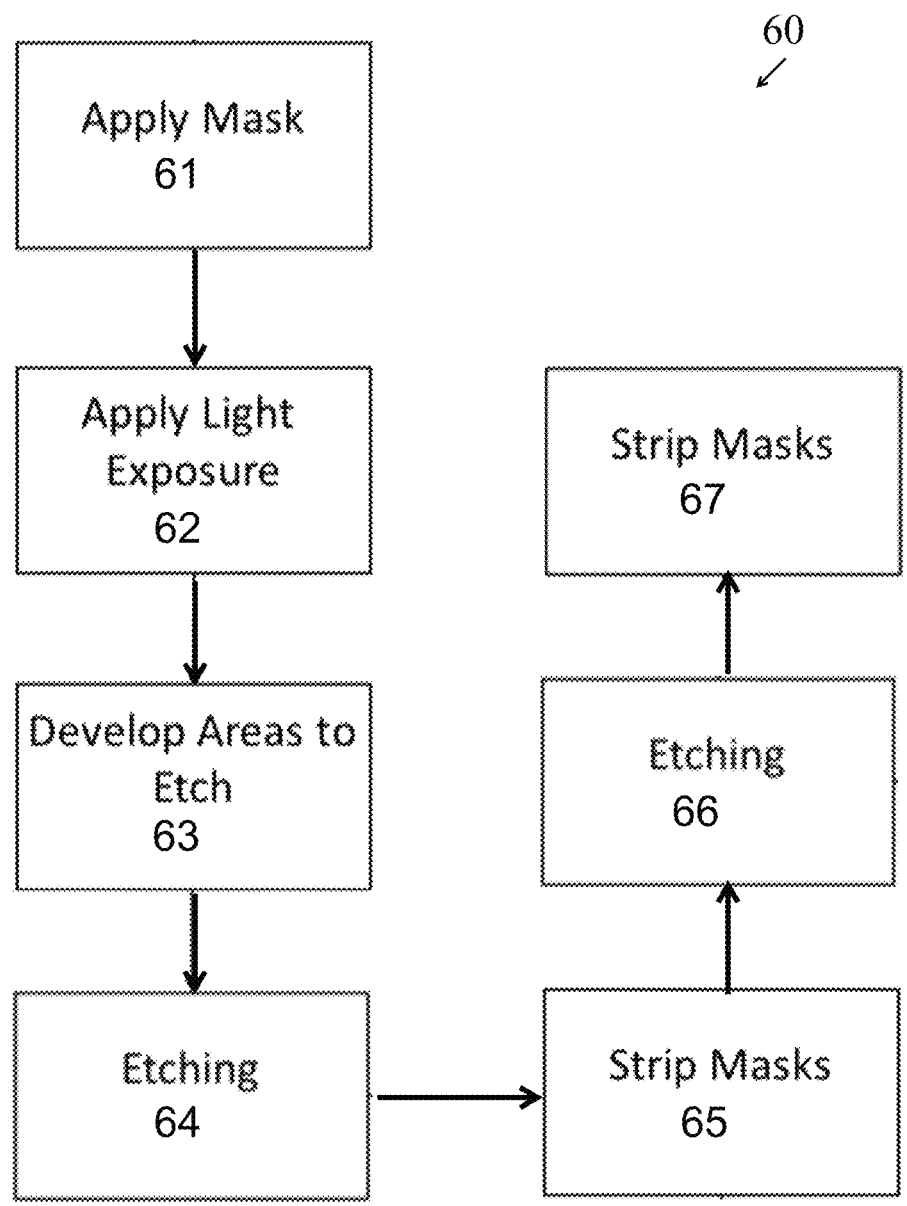
FIG. 6 illustrates a method for selectively rounding one or more edges of a needle, according to an example of this disclosure.

FIG. 6 illustrates a method 60 for selectively rounding one or more edges of a needle. The method 60 can be used to fabricate the one or more edges of a needle, such as those described herein; however, the needle can be formed by other methods. Likewise, the method 60 can be used to fabricate other needles having different profiles. The method 60 presumes the provision of a metal base, such as a sheet of metal.

The metal can be stainless steel, for example. In different examples, the thickness of the metal base may be less than about 1000 micrometers, such as less than about 500 micrometers, such as between about 250 micrometers and about 500 micrometers. However, in other examples, metal bases with thicknesses larger than 1000 micrometers or smaller than 250 micrometers may be used. In addition, a metal base may include beveling, such that etching is used to finish an edge rather than form an edge from metal base two generally parallel major surfaces. In such examples, metal bases many times thicker than 1000 micrometers are practical.

The method 60 includes applying 61 one or more masks to the metal base. The masks can be applied in various different ways. One type of mask can be applied as a dry film photoresist, in which an undeveloped film is placed on the metal base and then developed by light 62. The light can be a laser light which is directed only on those portions of the film corresponding to the sections of the metal base which are not to be etched. Alternatively, the light can be broadband light, such as broadband ultraviolet light.

At step 63, the broadband light is shown only on those sections of the film overlapping sections of the metal base which are not to be etched with use of a negative tone photoresist with use of a negative tone photoresist, the light for those sections to be etched blocked by a screen having a profile similar to the planned area of etching. Whether by laser, ultraviolet light, or other means, the film is hardened into a mask over those areas of the metal base which are not to be etched while other areas of the film are left unhardened. The hardening adheres the film to the metal base. Unhardened areas are then washed away, leaving a mask which protects particular areas of the metal base which are not to be etched while leaving exposed other areas of the metal base which are to be etched. Positive tone photoresist may be used as an alternative to negative tone photoresist.

The method 60 further includes etching 64. An etchant solution can be used to perform etching 64. An aqueous solution of ferric chloride can be used, for example, however other etching chemicals are possible. The etchant solution removes metal portions of the metal base from the exposed areas. The etchant solution typically does not react with the material of the mask and as such the etchant solution typically does not penetrate directly through the mask to remove metal directly underneath the mask, particularly when a solid mask is used with no discontinuities. The etchant solution can remove metal in a rapid manner by a chemical process similar to corrosion. The etchant solution can be sprayed on the metal base and/or the metal base can be dipped in etchant solution, amongst other options.

The method 60 further includes removal 65 of one, several or, all of the one or more masks previously applied 61. One or more masks can be scraped away and/or chemically removed such as with a solvent (e.g., an organic solvent in the case of a polymer-based mask).

The method further includes etching 66 the metal base. The etching 66 can be similar to the previous etching 64 step. The method 60 further includes a post etch 66 removal 67, or cleaning of the one or more edges of a needle. Edge fabrication from a metal base, according to the present methods, can be accomplished by etching alone. Edge fabrication according to the present methods can be accomplished without any mechanical machining of the needle. However, other portions of the needle may be mechanically machined.

One advantage of chemically selective rounded edges, as compared to mechanically machined edges, is that the chemically selective rounded edges can be in an optimally hardened state before etching and the etching will not change the hardened state of the metal (e.g., will not soften or otherwise change the grain structure of the metal). Mechanically machined edges typically soften during mechanical machining due to the heat generated by the mechanical machining. Mechanically machined edges must be re-hardened after mechanical machining. Thus, chemically selective rounded edges may be hardened only once.

Figure 7:
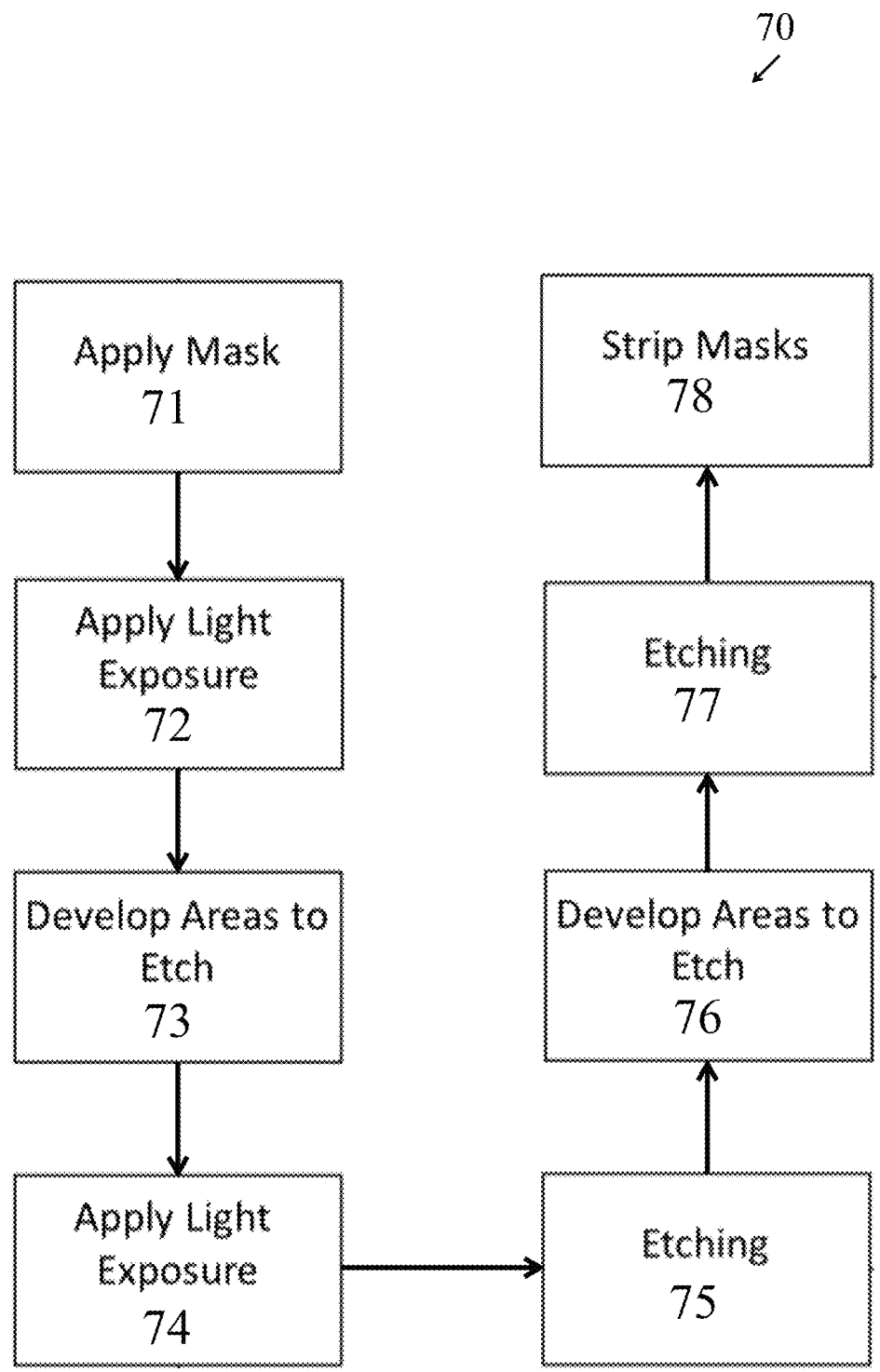
FIG. 7 illustrates an alternative method for selectively rounding one or more edges of a needle according to an example of this disclosure.

FIG. 7 illustrates an alternative method 70 for selectively rounding one or more edges of a needle. The method 70 can be used to fabricate the one or more edges of a needle, such as those described herein; however, the needle can be formed by other methods. Likewise, the method 70 can be used to fabricate other needles having different profiles. The method 70 presumes the provision of a metal base, such as a sheet of metal. The metal can be stainless steel, for example. In different examples, the thickness of the metal base may be less than about 1000 micrometers, such as less than about 500 micrometers, such as between about 250 micrometers and about 500 micrometers. However, in other examples, metal bases with thicknesses larger than 1000 micrometers or smaller than 250 micrometers may be used. In addition, a metal base may include beveling, such that etching is used to finish an edge rather than form an edge from metal base two generally parallel major surfaces. In such examples, metal bases many times thicker than 1000 micrometers are practical.

The method 70 includes applying 71 one or more masks to the metal base. The masks can be applied in various different ways. One type of mask can be applied as a dry film photoresist, in which an undeveloped film is placed on the metal base and then developed by light 72. The light can be a laser light which is directed only on those portions of the film corresponding to the sections of the metal base which are not to be etched. Alternatively, the light can be broadband light, such as broadband ultraviolet light. At step 73, the areas to be etched are developed. Specifically, the broadband light is shown only on those sections of the film overlapping sections of the metal base which are not to be etched with use of a negative tone photoresist with use of a negative tone photoresist, the light for those sections to be etched blocked by a screen having a profile similar to the planned area of etching.

Whether by laser, ultraviolet light, or other means, the film is hardened into a mask over those areas of the metal base which are not to be etched while other areas of the film are left unhardened. The hardening adheres the film to the metal base. Unhardened areas are then washed away, leaving a mask which protects particular areas of the metal base which are not to be etched while leaving exposed other areas of the metal base which are to be etched. Positive tone photoresist may be used as an alternative to negative tone photoresist. The method 70 further includes applying light exposure 74. The application of light exposure 74 can be similar to the previous applying light exposure 72 step. The second light exposure step 74 defines the edge rounding of the needle.

The method 70 further includes etching 75. An etchant solution can be used to perform etching 75. An aqueous solution of ferric chloride can be used, for example, however other etching chemicals are possible. The etchant solution removes metal portions of the metal base from the exposed areas. The etchant solution typically does not react with the material of the mask and as such the etchant solution typically does not penetrate directly through the mask to remove metal directly underneath the mask, particularly when a solid mask is used with no discontinuities. The etchant solution can remove metal in a rapid manner by a chemical process similar to corrosion. The etchant solution can be sprayed on the metal base and/or the metal base can be dipped in etchant solution, amongst other options.

The method 70 further includes developing areas to etch 76. The developing of areas to etch 76 can be similar to the previous developing areas to etch 73 step. The second light exposure step 74 defines the edge rounding of the needle. The method 70 further includes etching 77. The etching 77 can be similar to the previous etching 75 step. The second etching step 77 etches the selective rounded edges of the needle.

The method 70 further includes removal 78 of one, several or, all of the one or more masks previously applied. One or more masks can be scraped away and/or chemically removed such as with a solvent (e.g., an organic solvent in the case of a polymer-based mask).

Edge fabrication from a metal base, according to the present methods, can be accomplished by etching alone. Edge fabrication according to the present methods can be accomplished without any mechanical machining of the edge. However, other portions of the needle may be mechanically machined.

While multiple examples are disclosed, still other examples within the scope of the present disclosure will become apparent to those skilled in the art from the detailed description provided herein, which shows and describes illustrative examples. Accordingly, the drawings and detailed description are to be regarded as illustrative in nature and not restrictive. Features and modifications of the various examples are discussed herein and shown in the drawings. While multiple examples are disclosed, still other examples of the present disclosure will become apparent to those skilled in the art from the following detailed description, which shows and describes illustrative examples of this disclosure. Accordingly, the drawings and detailed description are to be regarded as illustrative in nature and not restrictive.

What is claimed is:

1. A chemically etched needle comprising:
a metal base having a first side and a second side;
a chemically etched blade at one end of the metal base and formed at an intersection of a distal diverging surface and a proximal diverging surface, wherein at least one of the diverging surfaces slopes inward towards the second side, and wherein the blade is formed through at least one variable permeability mask; and
a portion of the chemically etched needle comprising at least one of:
   a first rounded edge at an intersection of the second side of the chemically etched needle and the distal diverging surface;
   a second rounded edge at an intersection of the first side of the chemically etched needle and the distal diverging surface;
   a third rounded edge at an intersection of the second side of the chemically etched needle and the proximal diverging surface; and
   a fourth rounded edge at an intersection of the first side of the chemically etched needle and the proximal diverging surface;
the first, second, third, and fourth rounded edges being formed by etching the metal base through at least one mask.

2. The chemically etched needle of claim 1, wherein at least one of the proximal diverging surface and the distal diverging surface includes one or more concave portions formed by etching the metal base through at least one variable permeability mask.

3. The chemically etched needle of claim 2, wherein the at least one variable permeability mask includes a mask having a comb profile.

4. The chemically etched needle of claim 1, wherein the first side of the chemically etched needle and the second side of the chemically etched needle is not symmetric about a centerline of the metal base.

5. The chemically etched needle of claim 1, wherein the metal base is a stainless-steel metal base.

6. The chemically etched needle of claim 1, wherein said portion of the chemically etched needle includes the first rounded edge at the intersection of the second side of the chemically etched needle and the distal diverging surface, the first rounded edge being formed by etching the metal base through at least one variable permeability mask.

7. The chemically etched needle of claim 1, wherein said portion of the chemically etched needle includes the second rounded edge at the intersection of the first side of the chemically etched needle and the distal diverging surface, the second rounded edge being formed by etching the metal base through at least one variable permeability mask.

8. The chemically etched needle of claim 1, wherein said portion of the chemically etched needle includes the third rounded edge at the intersection of the second side of the chemically etched needle and the proximal diverging surface, the third rounded edge being formed by etching the metal base through at least one variable permeability mask.

9. The chemically etched needle of claim 1, wherein said portion of the chemically etched needle includes the fourth rounded edge at the intersection of the first side of the chemically etched needle and the proximal diverging surface, the fourth rounded edge being formed by etching the metal base through at least one variable permeability mask.

10. The chemically etched needle of claim 1, wherein a thickness of the metal base is less than about 1000 micrometers.

11. The chemically etched needle of claim 1, wherein a thickness of the metal base is less than about 500 micrometers.

12. The chemically etched needle of claim 1, wherein a thickness of the metal base is between about 250 micrometers and about 500 micrometers.

13. The chemically etched needle of claim 1, wherein at least one of the diverging surfaces includes one or more concave portions.

14. The chemically etched needle of claim 1, wherein said at least one of the first, second, third, and fourth rounded edges are formed concurrently with the chemically etched blade.

* * * * *